(12) United States Patent
Sigg et al.

(10) Patent No.: US 8,852,173 B2
(45) Date of Patent: Oct. 7, 2014

(54) METHODS AND SYSTEMS FOR PROVIDING THERAPIES INTO THE PERICARDIAL SPACE

(75) Inventors: Daniel C. Sigg, St. Paul, MN (US); Michael R. Ujhelyi, Maple Grove, MN (US); Mary M. Morris, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/273,521

(22) Filed: Oct. 14, 2011

(65) Prior Publication Data

US 2012/0035587 A1 Feb. 9, 2012

Related U.S. Application Data

(60) Division of application No. 11/000,538, filed on Dec. 1, 2004, now abandoned, which is a (Continued)

(51) Int. Cl.
*A61K 9/22* (2006.01)
*A61B 17/34* (2006.01)
(Continued)

(52) U.S. Cl.
CPC .. *A61M 5/14276* (2013.01); *A61B 2018/00357* (2013.01); *A61B 17/3478* (2013.01); *A61B 2017/003* (2013.01); *A61B 2018/00392* (2013.01); *A61B 2017/22077* (2013.01); *A61M 2205/3523* (2013.01); *A61B 2018/00291* (2013.01); *A61B 2017/3488* (2013.01); *A61B 2017/00247* (2013.01); *A61B 18/1492* (2013.01); *A61M 2005/1405* (2013.01); *A61B 2017/349* (2013.01); *A61B 17/3417* (2013.01); *A61B 2017/3484* (2013.01); *A61B 17/00234* (2013.01); *A61M 5/1723* (2013.01)

USPC .......................................................... 604/891.1

(58) Field of Classification Search
USPC ....................... 604/891.1, 93.01, 65; 607/2, 3
See application file for complete search history.

(56) References Cited

U.S. PATENT DOCUMENTS

| | | |
|---|---|---|
| 3,721,229 A | 3/1973 | Panzer |
| 4,263,679 A | 4/1981 | Erlendson |

(Continued)

FOREIGN PATENT DOCUMENTS

| | | |
|---|---|---|
| EP | 0487175 | 3/1991 |
| EP | 0672427 | 9/1995 |

(Continued)

OTHER PUBLICATIONS

Megson et al.; Expert Opin. Investig. Drugs (2002) 11(5):587-601.*

(Continued)

*Primary Examiner* — Kevin C Sirmons
*Assistant Examiner* — Deanna K Hall

(57) ABSTRACT

Methods and systems for transvenously accessing the pericardial space via the vascular system and atrial wall, particularly through the superior vena cava and right atrial wall, to deliver a pharmacologic agent, particularly a NO-donor drug, to the heart are disclosed. A proximal connector of an infusion catheter is coupled to an infusion pump, and a distal catheter segment having a distal infusion catheter lumen end opening is disposed in the pericardial space. The implantable infusion pump is operable in conjunction with an implantable ischemia monitor to monitor the ischemic state and trigger delivery or regulate the periodic delivery of the pharmacologic agent to optimally treat ischemia. The patient may operate a patient activator that the patient when feeling ischemia symptoms to transmit a signal that is received by the implantable infusion pump and triggers delivery of a bolus and/or continuous infusion.

22 Claims, 9 Drawing Sheets

Related U.S. Application Data continuation-in-part of application No. 10/606,908, filed on Jun. 26, 2003, now Pat. No. 7,207,988, which is a division of application No. 09/430,096, filed on Oct. 29, 1999, now Pat. No. 6,613,062.

(51) Int. Cl.
*A61M 5/142* (2006.01)
*A61M 5/172* (2006.01)
*A61B 18/00* (2006.01)
*A61B 17/00* (2006.01)
*A61B 17/22* (2006.01)
*A61B 18/14* (2006.01)
*A61M 5/14* (2006.01)

(56) References Cited

U.S. PATENT DOCUMENTS

| | | | |
|---|---|---|---|
| 4,285,347 A | | 8/1981 | Hess |
| 4,692,147 A | | 9/1987 | Duggan |
| 4,815,478 A | | 3/1989 | Buchbinder et al. |
| 4,884,567 A | * | 12/1989 | Elliott et al. ............ 606/126 |
| 4,946,457 A | | 8/1990 | Elliot |
| 4,987,897 A | | 1/1991 | Funke |
| 4,991,578 A | | 2/1991 | Cohen |
| 5,146,925 A | | 9/1992 | Snow |
| 5,199,428 A | | 4/1993 | Obel et al. |
| 5,269,326 A | | 12/1993 | Verrier |
| 5,305,745 A | | 4/1994 | Zacouto et al. |
| 5,330,496 A | | 7/1994 | Alferness |
| 5,330,497 A | | 7/1994 | Freitas et al. |
| 5,331,996 A | | 7/1994 | Ziehm |
| 5,336,252 A | | 8/1994 | Cohen |
| 5,344,439 A | | 9/1994 | Otten |
| 5,345,927 A | | 9/1994 | Bonutti |
| 5,368,040 A | | 11/1994 | Carney |
| 5,415,637 A | | 5/1995 | Khosravi |
| 5,454,790 A | | 10/1995 | Dubrul |
| 5,489,270 A | | 2/1996 | Van Erp |
| 5,564,434 A | | 10/1996 | Halperin et al. |
| 5,634,895 A | | 6/1997 | Igo et al. |
| 5,674,249 A | | 10/1997 | De Coriolis et al. |
| 5,678,572 A | | 10/1997 | Shaw et al. |
| 5,681,280 A | | 10/1997 | Rusk et al. |
| 5,713,867 A | | 2/1998 | Morris |
| 5,728,148 A | | 3/1998 | Bostrom et al. |
| 5,749,883 A | | 5/1998 | Halperin |
| 5,755,737 A | | 5/1998 | Prieve et al. |
| 5,759,202 A | | 6/1998 | Schroeppel |
| 5,797,870 A | | 8/1998 | March et al. |
| 5,800,451 A | | 9/1998 | Buess et al. |
| 5,810,735 A | | 9/1998 | Halperin et al. |
| 5,827,216 A | | 10/1998 | Igo et al. |
| 5,873,842 A | | 2/1999 | Brennen et al. |
| 5,900,433 A | | 5/1999 | Igo et al. |
| 5,928,260 A | | 7/1999 | Chin et al. |
| 5,931,810 A | | 8/1999 | Grabek |
| 5,935,098 A | | 8/1999 | Blaisdell et al. |
| 5,968,010 A | | 10/1999 | Waxman et al. |
| 5,972,013 A | | 10/1999 | Schmidt |
| 6,066,149 A | | 5/2000 | Samson et al. |
| 6,112,124 A | | 8/2000 | Loeb |
| 6,115,630 A | | 9/2000 | Stadler et al. |
| 6,146,338 A | | 11/2000 | Gardeski et al. |
| 6,156,009 A | | 12/2000 | Grabek |
| 6,162,195 A | | 12/2000 | Igo et al. |
| 6,200,303 B1 | | 3/2001 | Verrier et al. |
| 6,203,526 B1 | | 3/2001 | McBeth et al. |
| 6,206,004 B1 | | 3/2001 | Schmidt et al. |
| 6,231,518 B1 | | 5/2001 | Grabek et al. |
| 6,358,536 B1 | | 3/2002 | Thomas |
| 6,361,522 B1 | | 3/2002 | Scheiner et al. |
| 6,375,668 B1 | | 4/2002 | Gifford et al. |
| 6,423,051 B1 | | 7/2002 | Kaplan et al. |
| 6,438,408 B1 | | 8/2002 | Mulligan et al. |
| 6,501,983 B1 | * | 12/2002 | Natarajan et al. ............ 600/517 |
| 6,558,382 B2 | | 5/2003 | Jahns et al. |
| 6,592,552 B1 | | 7/2003 | Schmidt |
| 6,613,062 B1 | | 9/2003 | Leckrone et al. |
| 6,632,197 B2 | | 10/2003 | Lyon |
| 6,651,672 B2 | | 11/2003 | Roth |
| 6,795,732 B2 | | 9/2004 | Stadler et al. |
| 6,796,966 B2 | | 9/2004 | Thomas |
| 7,037,290 B2 | | 5/2006 | Gardeski et al. |
| 7,072,711 B2 | * | 7/2006 | Girouard et al. ............ 607/3 |
| 7,207,988 B2 | | 4/2007 | Lekrone et al. |
| 7,758,521 B2 | | 7/2010 | Morris |
| 8,000,807 B2 | | 8/2011 | Morris |
| 2002/0019623 A1 | * | 2/2002 | Altman et al. ............ 604/508 |
| 2002/0120205 A1 | | 8/2002 | Ferek-Petric |
| 2003/0045805 A1 | | 3/2003 | Sheldon et al. |
| 2003/0093104 A1 | | 5/2003 | Bonner |
| 2003/0100925 A1 | | 5/2003 | Pape et al. |
| 2003/0204181 A1 | | 10/2003 | Starkebaum |
| 2004/0024435 A1 | | 2/2004 | Leckrone |
| 2004/0087938 A1 | | 5/2004 | Leckrone et al. |
| 2004/0106954 A1 | | 6/2004 | Whitehurst et al. |
| 2004/0116848 A1 | | 6/2004 | Gardeski et al. |
| 2004/0167410 A1 | | 8/2004 | Hettrick |
| 2005/0154370 A1 | | 7/2005 | Sigg et al. |
| 2005/0165466 A1 | | 7/2005 | Morris |

FOREIGN PATENT DOCUMENTS

| EP | 0382621 | 5/1998 |
|---|---|---|
| WO | WO 97/42879 | 11/1997 |
| WO | WO 98/02209 | 1/1998 |
| WO | WO 00/07497 | 2/2000 |

OTHER PUBLICATIONS

Al-Sa'Doni et al., "S-Nitrosothiols: A Class of Nitric Oxide-Donor Drugs," Clinical Science, 2000; 98:507-520.

Jozkowicz et al., "Genetic Augmentation of Nitric Oxide Synthase Increases the Vascular Generation of VEGF," Cardiovascular Research, 2001; 51(4):773-783.

Megson et al., "Nitric Oxide Donor Drugs: Current Status and Future Trends," Expert Opin. Investig. Drugs, 2002; 11(5):587-601.

Ruel et al., "Inhibition of the Cardiac Angiogenic Response to Surgical FGF-2 Therapy in a Swine Endothelial Dysfunction Model," Circulation, 2003; 108 Suppl 1: II335-II340.

Yamamoto et al., "Nitric Oxide Donors (44565)," Proc. Soc. Exp. Biol. Med., 2000; 225(3):200-206.

* cited by examiner

METHODS AND SYSTEMS FOR PROVIDING THERAPIES INTO THE PERICARDIAL SPACE

This application is a divisional of U.S. patent application Ser. No. 11/000,538, filed on Dec. 1, 2004 now abandoned, which is a continuation-in-part of U.S. patent application Ser. No. 10/606,908, filed Jun. 26, 2003, now U.S. Pat. No. 7,207,988, which is a division of U.S. patent application Ser. No. 09/430,096, filed Oct. 29, 1999, now U.S. Pat. No. 6,613,062, all of which are incorporated herein by reference.

FIELD OF THE INVENTION

This invention relates generally to methods and systems for delivering a pharmacologic agent into the pericardial space to treat the heart, e.g., methods and systems that deliver a pharmacologic agent into the pericardial space upon detection of symptoms of ischemia.

BACKGROUND OF THE INVENTION

The human heart wall consists of an inner layer of simple squamous epithelium, referred to as the endocardium, overlying a variably thick heart muscle or myocardium and is enveloped within a multi-layer tissue structure referred to as the pericardium. The innermost layer of the pericardium, referred to as the visceral pericardium or epicardium, clothes the myocardium. The epicardium reflects outward at the origin of the aortic arch to form an outer tissue layer, referred to as the parietal pericardium, which is spaced from and forms an enclosed sac extending around the visceral pericardium of the ventricles and atria. An outermost layer of the pericardium, referred to as the fibrous pericardium, attaches the parietal pericardium to the sternum, the great vessels and the diaphragm so that the heart is confined within the middle mediastinum. Normally, the visceral pericardium and parietal pericardium lie in close contact with each other and are separated only by a thin layer of a serous pericardial fluid that enables friction free movement of the heart within the sac. The space (really more of a potential space) between the visceral and parietal pericardia is referred to as the pericardial space. In common parlance, the visceral pericardium is usually referred to as the epicardium, and epicardium will be used hereafter. Similarly, the parietal pericardium is usually referred to as the pericardium, and pericardium will be used hereafter in reference to parietal pericardium.

Access to the pericardial space is desirable in order to provide a variety of cardiac therapies, including delivery of therapeutic agents (defined herein as including genetic agents, biologic agents, and pharmacologic agents), placement of electrical medical leads for pacing, cardioversion, defibrillation or EGM monitoring, removal of pericardial fluid for diagnostic analysis, or other purposes (e.g. placement of chemical sensors). A variety of mechanisms have been developed for accessing the pericardial space, ranging from a simple puncture by means of a large bore needle to intricate catheter or cannula based systems provided with sealing and anchoring mechanisms.

Access to the pericardial space may be accomplished from outside the body by making a thoracic or sub-xiphoid incision to access and cut or pierce the pericardial sac. Access to the pericardial space from the exterior of the body, accomplished by passing a cannula or catheter type device through the chest wall and thereafter passing the cannula or catheter or a further instrument through the pericardium into the pericardial space, is disclosed in U.S. Pat. Nos. 5,827,216, 5,900,433, and 6,162,195 issued to Igo, U.S. Pat. No. 5,336,252 issued to Cohen, and U.S. Pat. Nos. 5,972,013, 6,206,004, 6,592,552 by Schmidt, for example. In certain cases the pericardial sac is cut by a cutting instrument as disclosed in U.S. Pat. Nos. 5,931,810, 6,156,009, and 6,231,518 issued to Grabek et al.

Alternatively, an elongated perforating instrument device is introduced from a skin incision or puncture by a transvenous or transarterial approach into the right or left heart chambers, respectively, and a cutting or piercing or penetrating mechanism at the distal end of the elongated perforating instrument is operated to penetrate through the atrial or ventricular wall of the right or left heart chamber into the surrounding pericardial space without perforating the pericardial sac. For example, a transvenous catheter provided with a hollow helical needle adapted to rotated and pierce through the wall of a right or left heart chamber to access the pericardial space to deliver pharmacologic agents is disclosed in U.S. Pat. No. 5,797,870 issued to March et al. A transvenous catheter introduced into the right ventricular chamber to provide access through the right ventricular wall to enable passage of an electrical medical lead into the pericardial space is disclosed in, U.S. Pat. No. 4,991,578 issued to Cohen, and U.S. Pat. No. 5,330,496 issued to Alferness, for example. It has also been proposed that a preferred site of penetration of catheters or electrical medical leads through the atrial wall into the pericardial space is within the right atrial appendage as disclosed in U.S. Pat. No. 5,269,326 issued to Verrier, U.S. Pat. No. 6,200,303 issued to Verrier et al and U.S. Pat. No. 5,968,010 issued to Waxman et al. Transvenous approaches through either of the inferior vena cava or the superior vena cava are disclosed in these patents.

It would be particularly desirable to facilitate access to the pericardial space to enable chronic delivery of pharmacologic agents to the heart as suggested in the above-referenced '326, '303, and '010 patents. In particular it is noted that the pericardial fluid provides an excellent medium for delivery of pharmacologic agents to the cardiac muscles and coronary vessels without distribution to other organs. Among the clinically significant pharmacologic agents (i.e., drugs) which could advantageously be delivered to the heart via the pericardial fluid are those that improve cardiac contractility (e.g., digitalis drugs, adrenergic agonists, etc.), that suppress arrhythmias (e.g., class I, II, III, and IV agents and specialized drugs such as amiodarone, which is particularly potent but has severe systemic side effects), that dilate coronary arteries (e.g., nitroglycerin, calcium channel blockers, etc.), that lyse clots in the coronary circulation (e.g., thrombolytic agents such as streptokinase or tissue-type plasminogen activator (TPA)) or that reverse symptoms of heart failure (e.g. beta-adrenergic blockers).

Examples of other pharmacologic agents which may be administered into the pericardial space include: agents to protect the heart pharmacologically from the toxic effects of drugs administered to the body generally for other diseases, such as cancer; antibiotics, steroidal and non-steroidal medications for the treatment of certain pericardial diseases; and growth factors to promote angiogenesis or neovascularization of the heart.

The delivery of further pharmacologic agents into the pericardial space is disclosed in the above-referenced '433 patent, wherein cardio-active or cardio-vascular active drugs are selected from vasodilator, antiplatelet, anticoagulant, thrombolytic, anti-inflammatory, antiarrhythmic, initropic, antimitotic, angiogenic, antiatherogenic and gene therapy bioactive agents. The approaches to the pericardial space include those disclosed in the above-referenced '326 patent or transthoracically, e.g., under the xiphoid process, i.e., by a sub-xiphoid surgical approach.

It is proposed in the '433 patent to deliver the pharmacologic agents into the pericardial space to treat or to prevent vascular thrombosis and angioplasty restenosis, particularly coronary vascular thrombosis and angioplasty restenosis, thereby to decrease incidence of vessel rethrombosis, unstable angina, myocardial infarction, and sudden death. In particular, it is proposed to deliver a congener of an endothelium-derived bioactive agent, more particularly a nitrovasodilator, representatively the nitric oxide donor agent sodium nitroprusside, to the pericardial space at a therapeutically effective dosage rate to abolish cyclic coronary flow reductions (CFR's) while reducing or avoiding systemic effects such as suppression of platelet function and bleeding. Particular congeners of an endothelium-derived bioactive agent include prostacyclin, prostaglandin $E_1$, and a nitrovasodilator agent. Nitrovasodilater agents include nitric oxide (NOX) and NOX donor agents, including L-arginine, sodium nitroprusside and nitroglycycerine. The so-administered nitrovasodilators are effective to provide one or more of the therapeutic effects of promotion of vasodilation, inhibition of vessel spasm, inhibition of platelet aggregation, inhibition of vessel thrombosis, and inhibition of platelet growth factor release, at the treatment site, without inducing systemic hypotension or anticoagulation. The administration of nitroglycerin intravenously has been demonstrated to reduce infarct size, expansion and complications in patients (Circulation. 1988 October; 78(4):906-19).

As set forth in commonly assigned U.S. Pat. No. 6,115,630 to Stadler et al, myocardial ischemia is a leading cause of human morbidity and mortality in developed countries. Myocardial ischemia involves oxygen starvation of the myocardium, particularly in the bulky left ventricular wall, which can lead to myocardial infarction and/or the onset of malignant arrhythmias if the oxygen starvation is not alleviated. Although myocardial ischemia is associated with the symptom of angina pectoris, the majority of episodes of myocardial ischemia are asymptomatic or "silent." Myocardial ischemia is caused by an imbalance of oxygen supply and oxygen demand. The diseased arteries are pathohistologically characterized by constriction in one or more section of a cardiac artery that is caused by vessel thrombosis, platelet aggregation, vessel spasm, angioplasty restenosis, and other conditions. This can cause to decreased oxygen supply, while exercise, stress or other conditions leading to increased tone of the sympathetic nervous system and/or increased blood levels of catecholamines can increase myocardial oxygen demand. As noted in the '630 patent, accurate and rapid detection of myocardial ischemia is the first essential step toward reducing morbidity and mortality from this often silent but deadly condition. Without the knowledge of the condition, it cannot be treated.

An ischemic event often causes the performance of the heart to be impaired and manifests itself through changes in the electrical (e.g. the electrocardiogram or EGM signal), functional (e.g., pressure, flow, etc.) or metabolic (e.g. blood or tissue oxygen, pH, etc.) parameters of the cardiac function. An ischemic event results in changes in the electrophysiological properties of the heart muscle that eventually manifest themselves as changes in the external ECG or internal EGM. The conventional approach to the detection of ischemia and infarction relies on analysis and interpretation of features of the ECG or EGM, e.g., the ST-segment, the T-wave or the Q-wave, to detect deviations from normal. Computer-based technology has been employed to monitor, display, and semi-automatically or automatically analyze the ischemic ECG changes. The above-referenced '630 patent sets forth improved methods of detecting ischemia from the EGM sensed across a plurality of sense electrodes.

In commonly assigned U.S. Pat. No. 5,199,428 to Obel et al, it is proposed that the detection of myocardial ischemia can be accomplished by sensing the patient's coronary sinus blood pH and/or oxygen saturation and comparing each to preset, normal thresholds. Blood pH or oxygen saturation sensors are located in the coronary sinus or a coronary vein to measure the dissolved oxygen and/or the lactic acid level of myocardial venous return blood. The measured blood oxygen saturation and/or blood pH and the ST segment deviation are compared to respective programmable thresholds reflecting clinical risk levels. When ischemia is confirmed, the disclosed system triggers burst stimulation of selected nerves until the measured blood gas and/or blood pH and/or ST segment returns to non-clinical risk levels.

For example, it has been proposed, as described in commonly assigned, co-pending U.S. patent application Ser. No. 10/002,338 filed Oct. 30, 2001, and Publication No. 2003/0083702 to employ various types of sensors including accelerometers, magnets, and sonomicrometers typically located in a blood vessel or heart chamber that respond to or move with mechanical heart function to derive a metric that changes in value over the heart cycle in proportion to the strength, velocity or range of motion of one or more of the heart chambers or valves. Such a mechanical function metric would complement the measurement of blood pressure and the EGM to more confidently determine the degree of change in a heart failure (HF) condition of the heart.

An implantable EGM monitor for recording the cardiac electrogram from electrodes remote from the heart as disclosed in commonly assigned U.S. Pat. No. 5,331,966 and PCT publication WO 98/02209 is embodied in the Medtronic® REVEAL® Insertable Loop Recorder having spaced housing EGM electrodes. More elaborate implantable hemodynamic monitors (IHMs) for recording the EGM from electrodes placed in or about the heart and other physiologic sensor derived signals, e.g., one or more of blood pressure, blood gases, temperature, electrical impedance of the heart and/or chest, and patient activity have also been proposed. In particular, the Medtronic® CHRONICLE® Implantable Hemodynamic Monitor (IHM) system comprises a CHRONICLE® Model 9520 IHM of the type described in commonly assigned U.S. Pat. No. 5,368,040 coupled with a Model 4328A pressure sensor lead that monitors the EGM of the heart and senses blood pressure within a heart chamber using a pressure sensing transducer of the type disclosed in commonly assigned U.S. Pat. No. 5,564,434. The CHRONICLE® Model 9520 IHM measures absolute blood pressure, and the patient is also provided with an externally worn Medtronic® Model No. 2955HF atmospheric pressure reference monitor of the type described in commonly assigned U.S. Pat. No. 5,810,735 to record contemporaneous atmospheric pressure values.

A further IHM is disclosed in commonly assigned U.S. Pat. No. 6,438,408 that measures a group of parameters indicative of the state of HF employing EGM signals, measures of blood pressure including absolute pressure P, developed pressure DP (DP=systolic P—diastolic P), and/or dP/dt, and measures of heart chamber volume (V) over one or more cardiac cycles. These parameters include: (1) relaxation or contraction time constant tau (τ); (2) mechanical restitution (MR), i.e., the mechanical response of a heart chamber to premature stimuli applied to the heart chamber; (3) recirculation fraction (RF), i.e., the rate of decay of PESP effects over a series of heart cycles; and (4) end systolic elastance ($E_{ES}$), i.e., the ratios of end systolic blood pressure P to volume V. These HF state parameters are determined periodically regardless of patient posture and activity level. However, certain of the parameters are only measured or certain of the data are only stored when the patient heart rate is regular and within a normal sinus range between programmed lower and upper heart rates. The parameter data is associated with a date and time stamp and with other patient data, e.g., patient activity level, and the associated parameter data is stored in IMD memory for retrieval at a later date employing conventional telemetry systems. Incremental changes in the parameter data over time, taking any associated time of day and patient data into account, provide a measure of the degree of change in the HF condition of the heart.

Methods and apparatus for developing estimates of the ventricular afterload derived from ventricular pressure measurements employing the CHRONICLE® Model 9520 IHM coupled with a Model 4328A pressure sensor lead are described in commonly assigned, co-pending U.S. patent application Ser. No. 10/376,064 filed Feb. 26, 2003. The estimates of the ventricular afterload can be used to quantify the current state of cardiovascular function, to discern changes in the state of cardiovascular function over time, and to select or alter a therapy delivered by an IMD to optimize cardiovascular function of patients experiencing HF, hypertension, and other clinical pathologies A system and method are disclosed in commonly assigned co-pending U.S. patent application Ser. No. 10/368,278 filed Feb. 18, 2003, for detecting mechanical pulsus alternans (MPA) as well as associated electrical alternans and other MPA episode data from ventricular pressure and EGM measurements employing the CHRONICLE® Model 9520 IHM coupled with a Model 4328A pressure sensor lead. The collected MPA episode trend data provides indicia related to the mechanical performance of the HF patients heart so that the response of the heart to drug or electrical stimulation therapies prescribed to reduce HF symptoms can be assessed.

It has also been proposed to detect ischemic conditions of the heart from EGM characteristics, particularly, ST segment elevation, and mechanical heart motion as measured by an accelerometer or changes in measured blood pressure, for example, as described in commonly assigned, co-pending U.S. Patent Application Publication Nos. US 2003/0045805 and US 2002/0120205.

It is therefore desirable to provide a system and method that detects an ischemic state and delivers a pharmacologic agent into the pericardial space to treat the ischemic state in an efficient manner.

It would also be desirable to provide a system and method that delivers NO-donors into the pericardial space to treat detected conditions of the heart.

BRIEF SUMMARY OF THE INVENTION

Accordingly, the present invention provides systems and methods that access the pericardial space and deliver a pharmacologic agent into the pericardial space to counter a detected ischemic state or other cardiac condition.

In preferred embodiments, the methods and systems of the present invention provide for transvenously accessing the pericardial space between a heart and its pericardium to deliver a pharmacologic agent to the heart from an implantable infusion pump (IIP). A proximal connector of an infusion catheter is coupled to the IIP, and a distal catheter segment having a distal infusion catheter lumen end opening is disposed in the pericardial space. The IIP delivers a bolus the pharmacologic agent into the pericardial space to treat or counter symptoms of a cardiac condition.

In one preferred embodiment, the infusion catheter is routed transvenously into the right atrium and through the right atrial wall in the atrial appendage to dispose the distal infusion catheter lumen end opening in the pericardial space. The routing may be effected employing a fixation catheter attached to the right atrial wall.

Preferably, the IIP is operable to detect a remotely transmitted therapy delivery command and to deliver a bolus of the pharmacologic agent. Advantageously, the patient may be provided with a "patient activator" that the patient can operate when feeling cardiac symptoms, e.g., ischemia symptoms, to transmit a signal that is received by the IIP and triggers delivery of the bolus.

In a further embodiment, the IIP is operable in conjunction with an implantable ischemia monitor to monitor the ischemic state and regulate the periodic delivery of the pharmacologic agent to optimally treat ischemia.

Preferably, the IIP is preferably programmable by the treating physician, and a baseline dosage correlated to a detected baseline ischemic state is programmed by the physician at implantation and from time to time during patient work-ups. The baseline dosage frequency of delivery may be intermittent at specified intervals or continuous. A dosage adjustment from baseline dosage, e.g., a dosage adjustment in bolus volume or frequency of delivery, takes place as a function of the difference between a currently measured ischemic state and the baseline ischemic state. A weighting or scale factor can be programmed by the physician into memory to adjust the function: A maximum dosage adjustment (positive and negative) from baseline dosage may also be programmed by the physician.

Preferably, the pharmacologic agent comprises NO-releasing or NO-donor drugs selected from the group consisting of nitric oxide (NOX) and NOX donor agents, preferably selected among nitroglycerin (also known as glyceryltrinitrate or GTN), isosorbide mononitrate (ISMN), sodium nitroprusside (SNP), a diazenium diolate (e.g. DETA/NO), NO Aspirins (NCX 4016 and nCX 4215), an S-Nitrosothiol (SNAP), and morpholinosydnonimime (SIN-1) or any other compound which either induces increased nitric oxide levels (e.g. L-arginine, other NO-donors) The delivery of NO-donor drugs advantageously treats a number of cardiac conditions, including but not limited to ischemia.

The detection may be accomplished by sensing a feature of the EGM of the heart, and detecting a characteristic of the sensed feature indicative of the ischemic state. Alternatively or additionally, the detection may be accomplished by use of sensors sensing one or more of blood pH and blood oxygen saturation in the coronary sinus or blood pressure and blood flow in the heart and detecting a value indicative of the ischemic state. The ischemic state can be determined as a composite of the detected sensor and EGM signals.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS OF THE INVENTION

In the following detailed description, references are made to illustrative embodiments of methods and apparatus for carrying out the invention. It is understood that other embodiments can be utilized without departing from the scope of the invention.

Implantable drug pumps having drug reservoirs that can be refilled through ports accessed transcutaneously and coupled with catheters extending from the reservoir to a delivery site have been developed or proposed to deliver a variety of drugs. The Medtronic® SynchroMed® Infusion System approved for certain clinical uses comprises an Implantable Infusion Pump (IIP) coupled to a catheter. The battery powered IIP can be advantageously programmed to frequently or continuously deliver drug boluses of drugs that have a short duration of activity directly to an efficacious site. The IIP is surgically implanted subcutaneously under the skin such that the refill port is directed outward. The IIP reservoir can be refilled as necessary. Adverse side effects are reduced and the mental and physical states of many patients are improved by the automatically administered drug therapy. It is not necessary to rely upon the patient to comply with the prescribed regimen.

Figure 1:
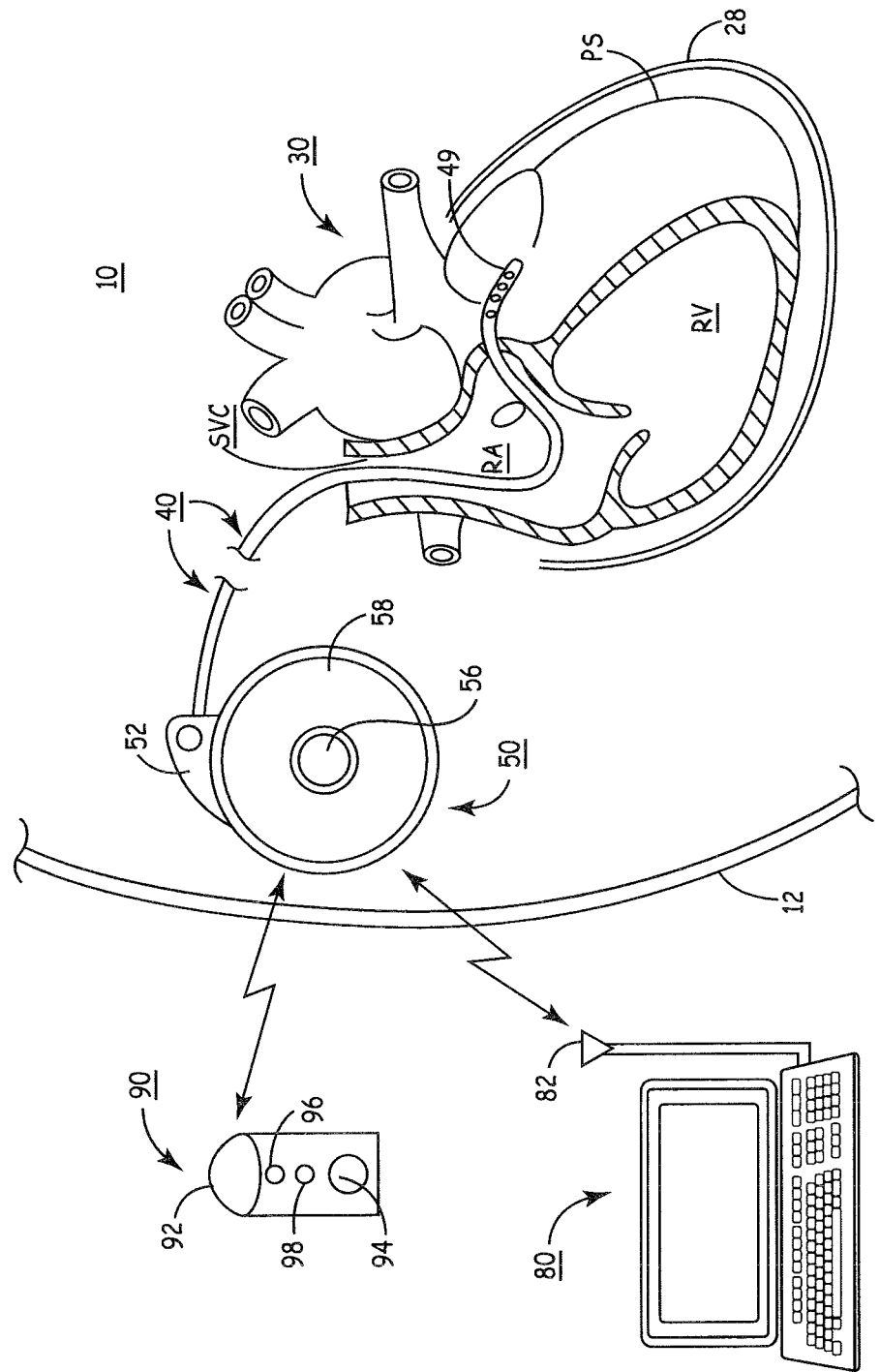
FIG. 1 is a schematic illustration of an IIP implanted subcutaneously within the patient's body coupled to an infusion catheter to deliver a bolus and/or continuous infusion of a pharmacologic agent, the bolus and/or continuous infusion programmed through use of an external programmer, into the pericardial space in response to an external patient activator trigger signal to counter an ischemic state detected by the patient.
Figure 2:
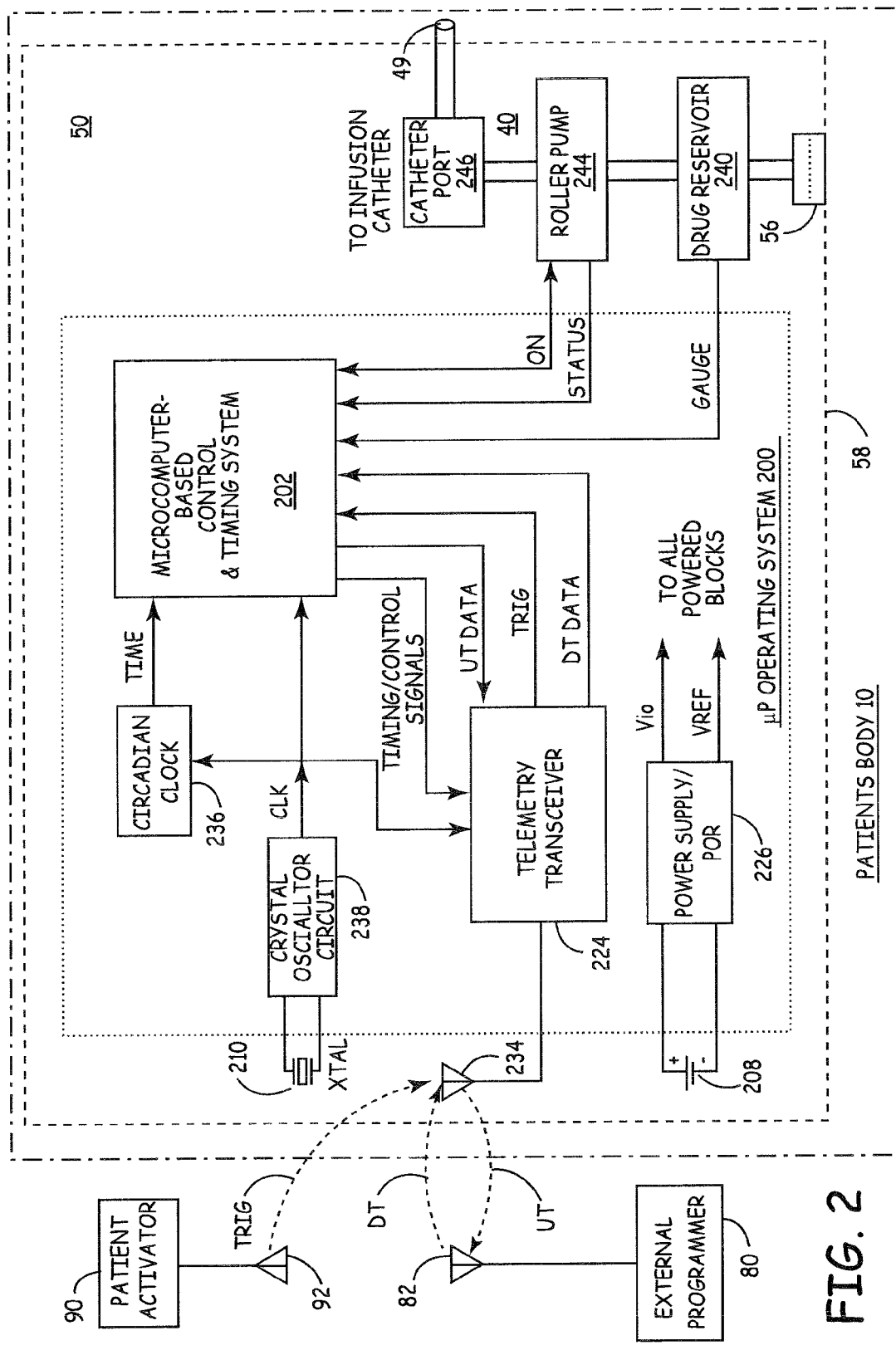
FIG. 2 is a schematic illustration of the operating system of the IIP of FIG. 1 in relation to the external programmer and patient activator.

One embodiment of an exemplary IIP system in which the present invention can be implemented is depicted in FIGS. 1 and 2 comprising an IIP 50 and infusion catheter 40 implanted in the patient's body 10 and an external programmer 80 and patient activator 90 operated by the patient. The IIP 50 communicates with the external programmer 80 through uplink telemetry (UT) and downlink telemetry (DT) transmissions through the patient's skin 12. The patient activator 90 can be operated by the patient to send a trigger (TRIG) signal through the patient's skin 12 to cause the IIP 50 to deliver a bolus of the pharmacologic agent.

In FIG. 1, the IIP 50 includes the infusion catheter 40 coupled at a proximal end to a fitting or connector 52 of the IIP housing 58 and extending into the pericardial space PS of heart 30 enclosed by pericardial sac or pericardium 28. The heart 30 and the surrounding pericardial sac 28 are cut away in part to expose the epicardium and the right heart chambers or the right atrium (RA) and the right ventricle (RV) (separated by the tricuspid valve). Venous blood drains into the RA through the superior vena cava (SVC) and the inferior vena cava (not shown). The RA appendage 32 extends somewhat laterally of the axis of the RA between the SVC and tricuspid valve.

Figure 4:
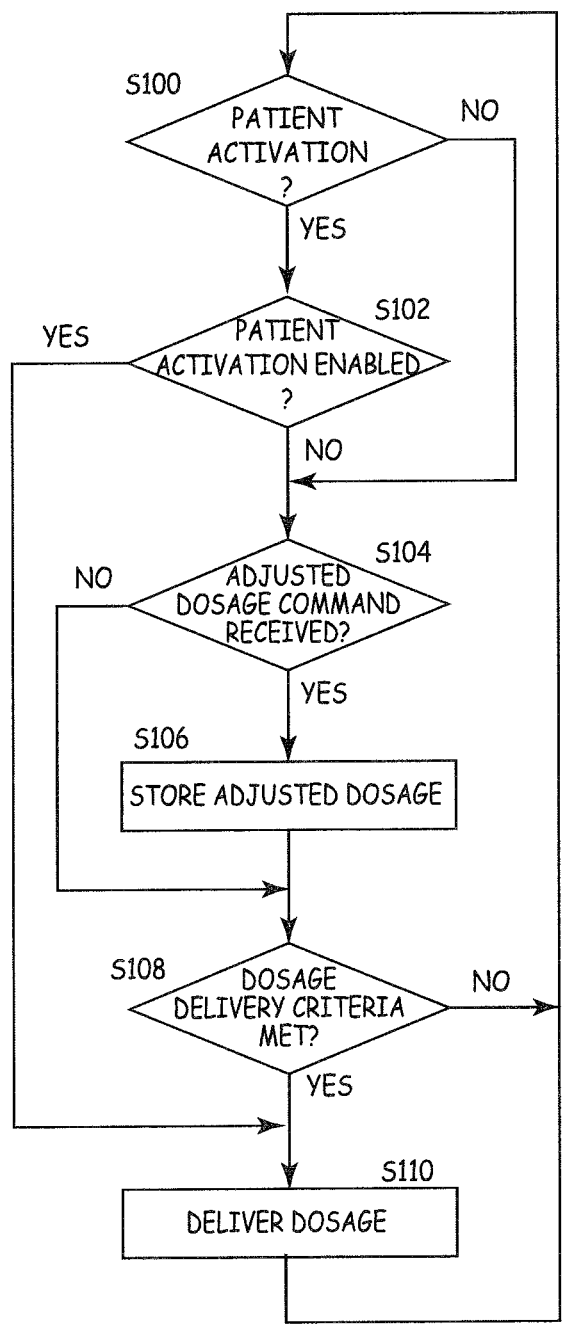
FIG. 4 is a simplified flow chart illustrating the operation of the system of FIGS. 1 and 2.

The infusion catheter 40 is illustrated in greater detail in FIG. 4 and comprises an elongated therapeutic catheter body 44 extending between a proximal fluid connector 42 and a therapeutic catheter body distal end 46. The fluid connector 42 is shaped and adapted to be coupled to the fluid connector 52 of the IIP 50 for chronic dispensation of drugs or agents from a reservoir of an IIP 50 into the pericardial space PS. A fluid transmitting lumen 48 extends from a proximal lumen end opening at the fluid connector 42 and one or more delivery lumen exit ports 49 at or near the therapeutic catheter body distal end 46. Fluid transmitting lumen 48 may function as a through lumen for over the wire advancement of the therapeutic catheter body 44 over a guidewire that is first passed through the atrial wall if a delivery lumen exit port 49 is axially aligned with fluid transmitting lumen 48.

The infusion catheter 40 is preferably advanced via the venous system draining through the superior vena cava into the right atrium, then deflected into the atrial appendage and through the right atrial wall to dispose the delivery lumen exit ports 49 in the pericardial space PS. The instruments and techniques disclosed in commonly assigned Published Patent Application No. 2004/0087938 A1 and U.S. Pat. No. 6,613, 062 to Leckrone et al may be employed to dispose the distal segment of the infusion catheter 40 in the pericardial space PS.

As depicted in commonly assigned U.S. Patent Application Publication No. 2003/0204181, the IIP housing 58 encloses an electronic control or operating system depicted in FIG. 2 including a control module 200 and associated electrical and mechanical components. The external programmer 80 and the patient activator 90 are also shown schematically in FIG. 2 disposed outside the patient's skin 12.

The mechanical components include a drug reservoir 240 associated with a resealable drug fill port 56 in the housing 58 and an outlet to a peristaltic roller pump 244. A bellows (not shown), associated with a gas-filled pressure chamber (not shown), applies a constant pressure against the drug reservoir 240 and the volume of drug within the drug reservoir 240. The catheter port 246 is coupled to the output of the peristaltic roller pump 246, and the roller pump 246 is periodically energized by an output signal of the circuit module 200 to deliver a dosage of the pharmacologic agent into the pericardial space through the infusion catheter 40. After subcutaneous implantation, a hypodermic needle is inserted through the patient's skin 12 and then through the resealable membrane of port 56 to fill the drug reservoir 240 with the pharmacologic agent.

Figure 3:
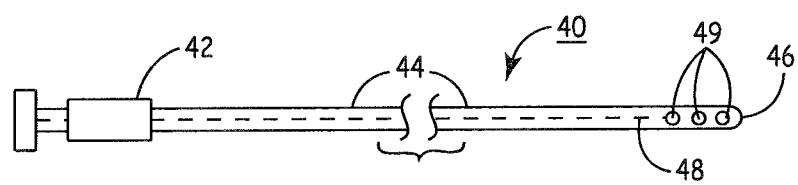
FIG. 3 is a schematic illustration of an exemplary infusion catheter usable in the practice of the present invention.

The control module 200 is also coupled to a battery or batteries 208, an RF telemetry antenna 234, and a piezoelectric crystal 210. The control module 200 has a system architecture that is constructed about a microcomputer-based control and timing system 202 that varies in sophistication and complexity depending upon the type and functional features incorporated therein. The micro-computer-based IIP control and timing system 202 can be similar to the microcomputer circuit 114 of the IHM 52 described above with respect to FIG. 3. The functions of microcomputer-based IIP control and timing system 202 are controlled by firmware and programmed software algorithms stored in RAM and ROM including PROM and EEPROM and are carried out using a CPU, ALU, etc., of a typical microprocessor core architecture.

Power levels and signals are derived from battery 208 by the power supply/POR circuit 226 having power-on-reset (POR) capability to power the roller pump 244 and the other components of the circuit module 200. The power supply/POR circuit 226 provides one or more low voltage power Vlo and one or more VREF sources. Not all of the conventional interconnections of these voltage sources and signals with the circuitry of the IIP control module 200 are shown in FIG. 2.

In certain IIPs, an audible patient alert warning or message can be generated by a transducer when driven by a patient alert driver to advise of device operations, e.g., confirmed delivery of a bolus or dosage of pharmacologic agent, or the battery depletion level to warn of a depleted battery state or depletion of the pharmacologic agent in reservoir 240.

Current electronic IIP circuitry of control module 200 employs clocked CMOS digital logic ICs that require a clock signal CLK provided by a piezoelectric crystal 210 and system clock 238 coupled thereto. In FIG. 2, each CLK signal generated by system clock 238 is routed to all applicable clocked logic of the microcomputer-based control and timing system 202 and to the telemetry transceiver I/O circuit 224 and the circadian or real time clock 236. The crystal oscillator 238 provides one or more fixed frequency system clock or CLK signal that is independent of the battery voltage over an operating battery voltage range for system timing and control functions and in formatting uplink telemetry signal transmissions in the telemetry I/O circuit 224. The real-time or circadian clock 134 driven by system clock 238 that provides a time of day signal to the microcomputer-based timing and control system 202.

The telemetry transceiver 224 coupled to the RF telemetry antenna 234 enables UT and DT telemetry capabilities with a remotely located external medical device, e.g., programmer 80, or a more proximal external medical device carried on the patient's body 10, or another IMD in the patient's body 10. During an UT transmission, the external RF telemetry antenna 82 of programmer 80 operates as a telemetry receiver antenna, and the IIP RF telemetry antenna 234 operates as a telemetry transmitter antenna. Conversely, during a DT transmission, the external RF telemetry antenna 82 operates as a telemetry transmitter antenna, and the IIP RF telemetry antenna 234 operates as a telemetry receiver antenna.

In general terms, the operation of the roller pump 244 can controlled through resident software and firmware in the microcomputer-based control and timing system 202 in a general manner similar to that described in commonly assigned U.S. Pat. No. 4,692,147. The frequency and volume of each bolus or dosage of pharmacologic agent delivered into the pericardial space can be governed by DT transmitted dosage commands that are stored in RAM. Data related to the delivery of dosages of pharmacologic agent can be stored in RAM within the microcomputer-based control and timing system 202 and UT transmitted to the programmer 80 in a telemetry session initiated by a medical care provider.

There are a number of ways that the IIP 50 can employed to dispense pharmacologic agent into the pericardial space PS in accordance with the various aspects of the invention. First, a fixed amount or bolus or dosage can be dispensed at predetermined timed intervals over the entire 24 hour day, that is once a day or more than once a day to maintain a relatively uniform level of pharmacologic agent in the pericardial space. Or, a bolus or dosage of pharmacologic agent into the pericardial space PS may be delivered at specific times as timed out by the circadian clock 236.

It is expected that the patient's physician would develop a conservative delivery regimen and use the programmer 80 to DT transmit the delivery times or delivery delay and bolus or dosage quantities. The symptoms of ischemia or pathologies associated with ischemia would be monitored, and the physician would periodically adjust the bolus or dosage depending upon the observed response or lack of response.

Optionally, the patient can be provided with the patient activator 90 to command the delivery of a bolus pharmacologic agent into the pericardial space PS. Suitable patient activators can communicate with IMDs, e.g., IIP 50, through the use of digitally encoded RF telemetry, infrared, acoustic pulsed, or magnetic signals that pass through the patient's skin 12. Preferably, the patient activator 90 is of the type disclosed in commonly assigned U.S. Pat. No. 5,755,737 or in U.S. Pat. Nos. 5,674,249 and 4,263,679 that communicate with the IIP 50 via RF DT transmissions through the patient's skin 12 between the patient activator antenna 92 and the IIP RF antenna 234.

For simplicity, the depicted exemplary patient activator 90 includes a battery powered RF telemetry transmitter conforming to the RF telemetry protocol employed in RF telemetry between the RF telemetry transceiver 224 and the telemetry transceiver within the programmer 80. The patient activator 90 preferably includes a button 94 to be depressed by the patient to cause an RF activation or TRIG signal to be emitted from the RF antenna 92 that is received by the RF telemetry transceiver 224. A first light, e.g., an LED 96, lights up when the TRIG signal is transmitted. A second light, e.g., LED 98, may be provided to indicate patient activator battery status.

The TRIG signal is received via RF antenna 234 and transmitted through RF telemetry transceiver 224 to the microcomputer-based control and timing system 202. In accordance with this aspect of the present invention, a motivated and competent patient provided with a patient activator 90 can transmit the TRIG signal and command the control and timing system 202 to deliver a bolus or dosage of pharmacologic agent when the patient experiences symptoms or preceding an activity that might cause symptoms, e.g., angina pectoris.

The frequency of delivery or discharge of dosages of pharmacologic agent can be limited within a delivery delay time window started by any delivery earlier initiated by the patient. In other words, the receipt of a TRIG command from the patient activator 90 would initiate delivery of the bolus of pharmacologic agent and also start a delivery delay timer that would have to time out before the control and timing system 202 can respond to any further TRIG commands initiated by the patient's use of the magnet patient activator 90.

The delivery of pharmacologic agent into the pericardial space (PS) is alternatively controlled in a variety of ways. The general operation of a drug delivery system including the IIP 50, the programmer 80, and the patient activator 90 is set forth in FIG. 3. During normal operation, the drug dosage is programmed or set by the physician and stored in memory of the microcomputer-based timing and control system 202. Thus, a revised or adjusted dosage that is received from external programmer 80 is stored in memory of the microcomputer-based timing and control system 202 in step S106 when such a dosage command is received as determined in step S104. The adjusted dosage is then employed in steps S108 and S110 until a further adjusted dosage is received and stored in steps S104 and S106. The dosage delivery algorithm determines if dosage delivery criteria are met in step S108, and the dosage is delivered in step S110 when the dosage delivery criteria are met. The baseline dosage frequency of the dosage delivery criteria can be continuous or intermittent.

If the patient is competent, the physician enables the patient activation function within programmed limits, e.g., how frequently a dosage may be delivered, both automatically and in response to patient activation, and the maximum dosage volume or bolus that can be delivered in a given time period. A drug dosage is delivered in step S110 when the patient activation is detected in step S100 and patient activation is so enabled as determined in step S102.

Thus, the drug dosage is delivered in step S110 from time to time or continuously, depending upon the programmed or adjusted delivery frequency, when the delivery criteria are met in step S108 in the absence of either a patient activation or a received dosage command in steps S100-S106. In the simplest operating mode and embodiment of the invention, only steps S108 and S110 are performed between refills of the drug dispenser reservoir and patient work-ups by the attending physician.

As noted above, a variety of implantable hemodynamic monitors (IHMs) for recording the EGM from electrodes placed in or about the heart and other physiologic sensor derived signals, e.g., one or more of blood pressure, blood gases, temperature, electrical impedance of the heart and/or chest, and patient activity have been proposed in the prior art. The present invention contemplates monitoring of the ischemic state of the patient employing any appropriate monitoring system and technology and modulating or regulating the delivery of the pharmacologic agent into the pericardial space PS.

Figure 5:
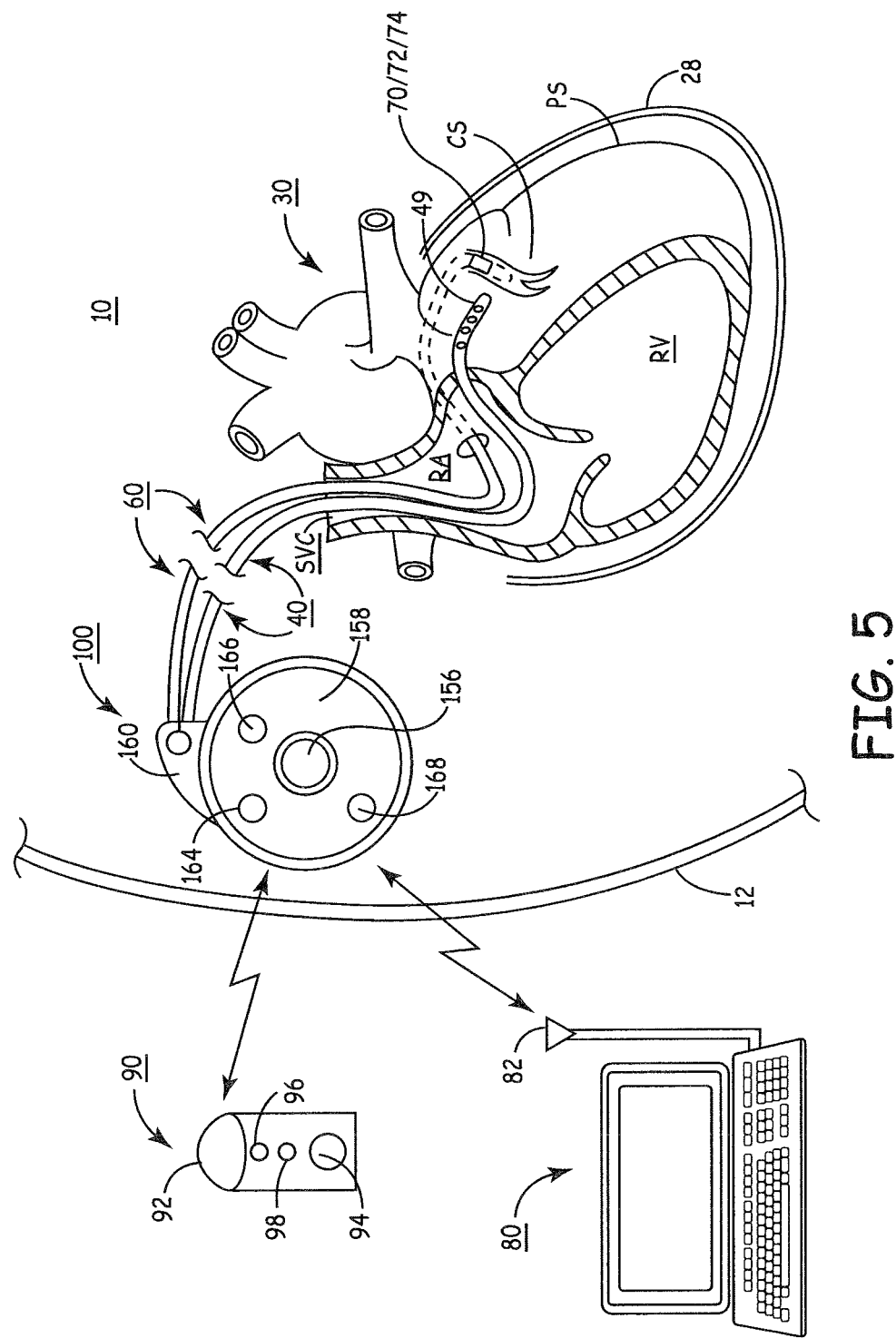
FIG. 5 is a schematic illustration of a combined IIP and ischemia monitor, programmed through use of an external programmer, implanted subcutaneously within the patient's body, coupled to an ischemia detection lead enabling detection of an ischemic state and an infusion catheter to deliver a bolus of a pharmacologic agent upon detection of the ischemic state or in response to an external patient activator trigger signal into the pericardial space to counter the ischemic state.
Figure 6:
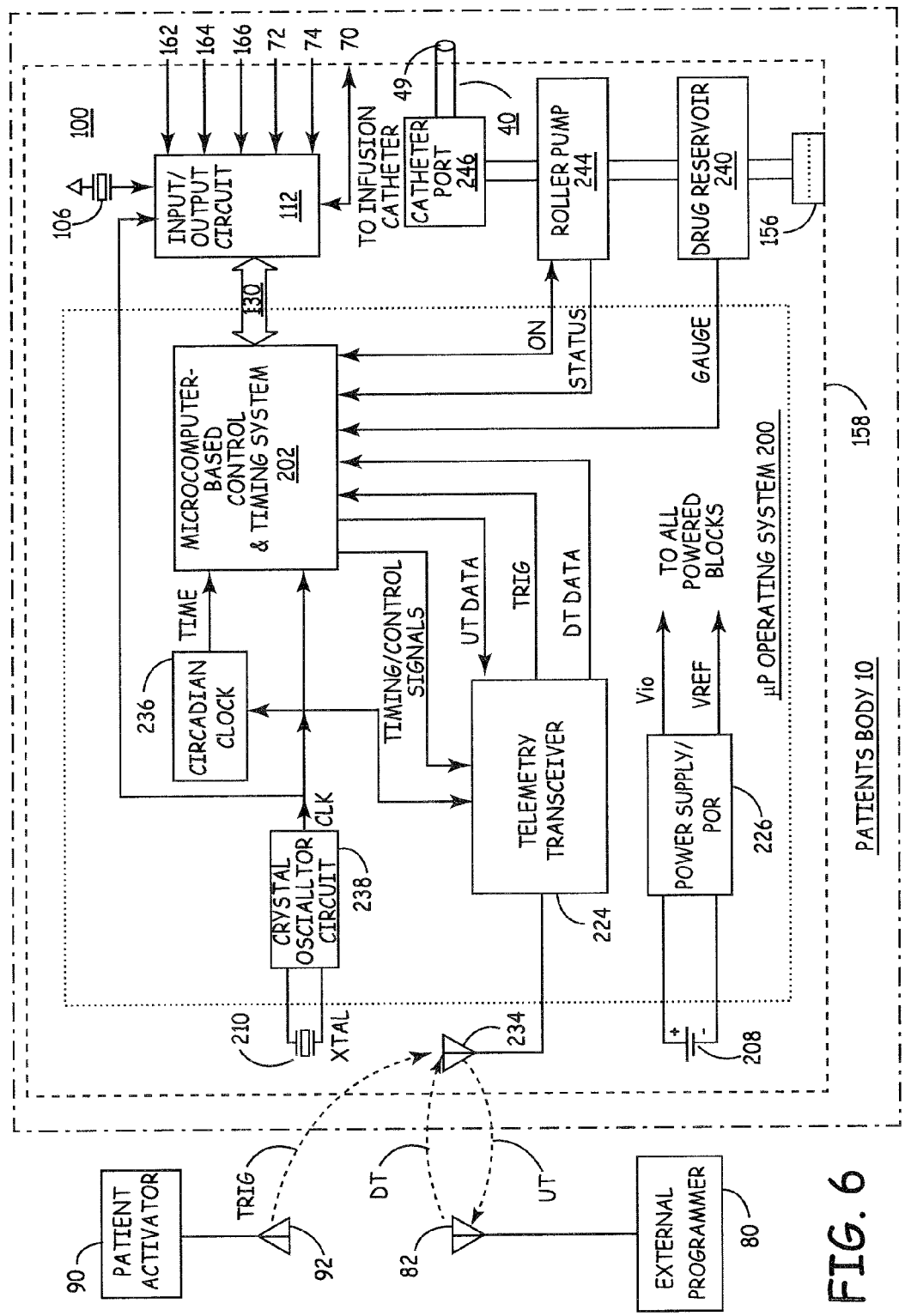
FIG. 6 is a schematic illustration of the operating system of the IIP of FIG. 4 in relation to the external programmer and patient activator with the infusion catheter extending through the right atrial wall into the pericardial space.

Thus, a still further exemplary IIP system in which the present invention can be implemented is depicted in FIGS. 5 and 6 comprising a combined ischemia monitor (IM) and IIP 100 coupled via connector 160 to the infusion catheter 40 and to an ischemia monitoring lead 60 implanted in the patient's body 10. The IM/IIP 250 communicates by RF telemetry with external programmer 80 via UT and DT transmissions as described above. The IM/IIP 250 optionally communicates with the patient activator 90 operated by the patient as described above with respect to FIGS. 1-3. An exemplary ischemia monitoring lead 60, depicted in greater detail in FIG. 7, supports a physiologic sensor and one or more sense electrode for sensing the EGM that are adapted to be disposed in the coronary sinus CS as shown in FIG. 5. The IM/IIP 250 operates in accordance with the method depicted in FIG. 8 to dispense a bolus of pharmacologic agent into the PS through the delivery lumen of the infusion catheter 40. The pharmacologic agent is dispensed from a reservoir within housing 158, and the reservoir is refilled through port 156 in the manner described above.

Figure 8:
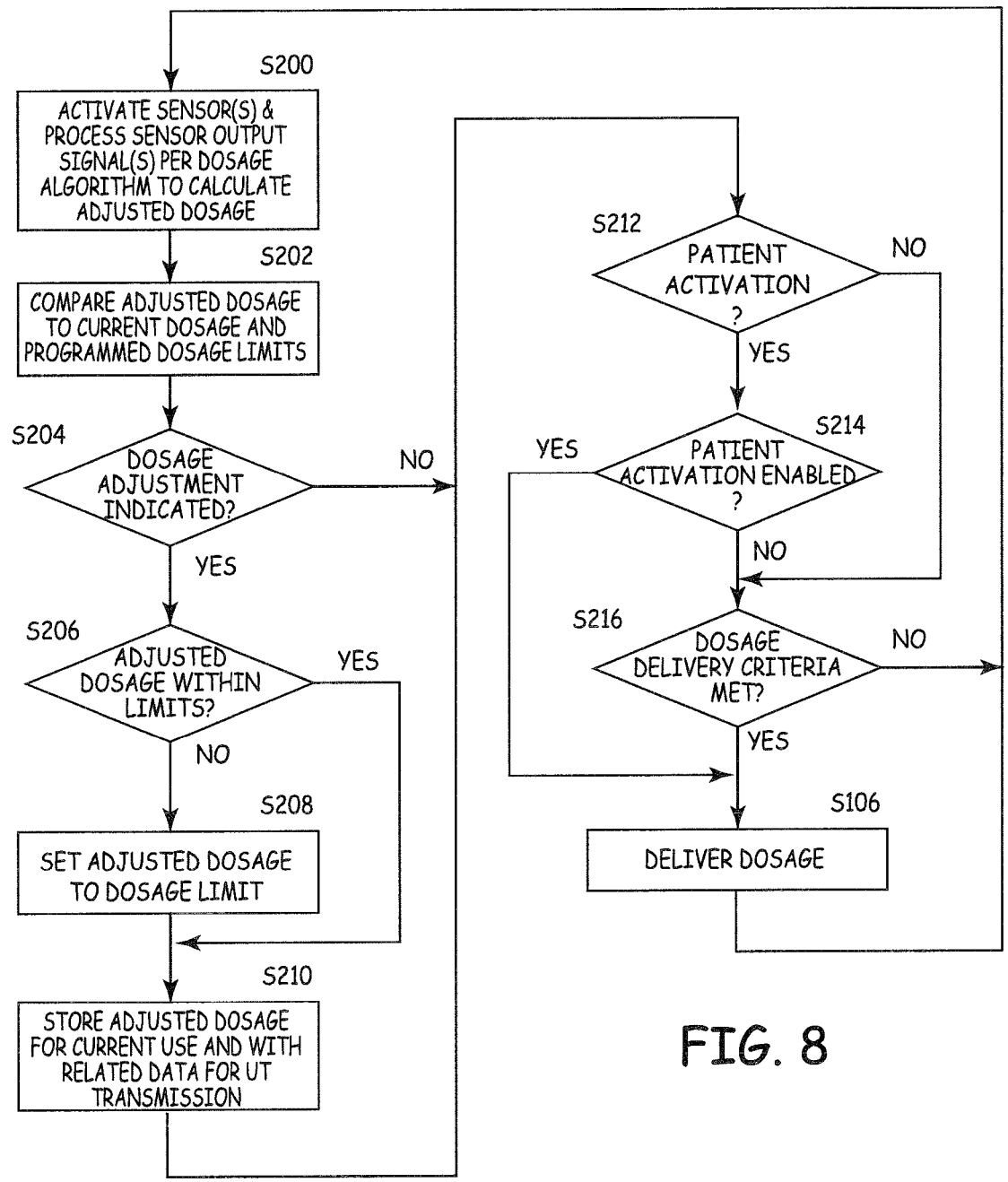
FIG. 8 is a simplified flow chart illustrating the operation of the system of FIGS. 5 and 6.

In this embodiment, the IM/IIP 100 further comprises electrical circuitry and components for deriving near field and/or far field EGM signals and one or more physiologic sensor signal and processing the signals in the manner depicted in FIG. 8 to determine an ischemic state to trigger or modulate the delivery of the pharmacologic agent through the infusion catheter 40 into the PS surrounding heart 30. For example, the IM/IIP housing 158 supports sense electrodes 162, 164, 166 arranged in an orthogonal array. The far field EGM can be detected from selected pairs of the electrodes 162, 164, 166 so that ST segment changes indicative of ischemia can be detected by sense circuitry of the operating system in the manner disclosed in the above-referenced '630 patent, for example. Moreover, the operating system responds to physiologic signals and/or near field EGM signals detected, for example, in the coronary sinus CS and conducted through the ischemia monitoring lead 60 to the operating system depicted in FIG. 6.

Figure 7:
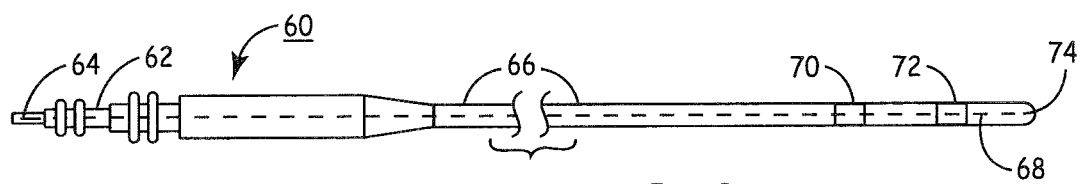
FIG. 7 is a schematic illustration of an exemplary ischemia monitoring lead usable in the practice of the present invention.

Turning to FIG. 7, an exemplary ischemia monitoring lead 60 is formed of an elongated lead body 66 extending between a proximal lead connector comprising a connector ring 62 and a connector pin 64 and a distal tip sense electrode 74. The proximal lead connector is shaped and adapted to be inserted into a bore of the connector 160 of the subcutaneously implanted IM/IIP 100. A proximal ring shaped sense electrode 72 and a physiologic sensor 70 are disposed along the elongated lead body 66 proximal to the distal tip sense electrode 64.

As shown in FIG. 5, the lead body 66 is adapted to be advanced through the venous system, the SVC, the RA, and the ostium of the CS to dispose the distal segment of the lead body 66 supporting the physiologic sensor 70 and the sense electrodes 72 and 74 in the CS or a vein branching from the CS. A lead lumen 68 extends from a proximal lumen end opening axially through connector pin 64 through the length of the lead body 66 and either terminates at extends axially through tip pace/sense electrode 64 to function as a stylet lumen to receive a stylet to advance the distal segment of the lead body into the CS or a through lumen for over the wire advancement of the lead body 66 over a guidewire placed in the CS.

In this location, the physiologic sensor 70 may comprise one or more chemical/biochemical sensor selected from the group consisting of a blood/extracellular tissue gas saturation sensor sensitive to changes in $pCO_2$ and $pO_2$ signifying ischemia, a blood pH sensor sensitive to pH and lactate changes signifying ischemia, and sensors capable of detecting myocardial enzyme leakage-troponin isoforms or creatine kinase or lactate dehydrogenase that are indicative of ischemia. Lead conductors extend within lead body between the proximal connector ring 62 and pin 64 and the sense electrodes 72 and 74, respectively, and the physiologic sensor 70. The signals on the lead conductors may be multiplexed in time to enable readout of the sensor and EGM signals.

It should be understood that the depicted physiologic sensor 70 disposed in the CS in FIG. 5 is merely exemplary of one location of a chemical/biochemical or chemical sensor in deriving sensor signals indicative of an ischemic state. The ischemia monitoring lead 60 can alternatively be routed into the pericardial space PS to dispose the EGM sense electrodes 72 and/or 74 and the chemical/biochemical physiologic sensor 70 therein. It will be understood that the ischemia monitoring lead 60 and the infusion catheter 40 may be combined to so dispose the sense electrodes 72 and/or 74 and/or physiologic sensor 70 in the pericardial space PS.

It will also be understood that a $pO_2$ sensor can be disposed into the myocardium to detect blood gas changes indicative of ischemia state and other cardiac conditions. Furthermore, other ischemia or cardiac condition sensors on sensor leads and disposed in use elsewhere in or about the heart may be substituted for physiologic sensor 70.

For example, a blood pressure sensor can be disposed in the right or left ventricular chamber to develop right ventricular pressure (RVP) signals or left ventricular pressure (LVP) signals, respectively, from which +dP/dt and/or an acute fall in RVP or LVP can be detected that is indicative of a worsening ischemic state. Alternatively, the blood pressure sensor may be disposed in the right atrial chamber to detect changes in right atrial pressure (RAP) indicative of a higher filling pressure. The physiologic sensor 70 and the sense electrode 72 may be combined so that ischemia monitoring lead 60 functions in the manner of the combined EGM and pressure sensing lead disclosed in commonly assigned U.S. Pat. No. 5,564,434 to Halperin et al.

Alternatively, the EGM sense electrodes 72 and/or 74 and/or physiologic sensor 70 may be located in any suitable cardiac vessel or chamber and be configured to develop blood flow signals indicative in ischemia state and other cardiac conditions.

Moreover, it will be understood that changes in heart volume, ejection fraction and segment shortening indicative of an ischemic state or other cardiac condition may be derived from the output signals of a plurality of accelerometers, magnets or sonomicrometers arrayed about the heart as described in the above-referenced commonly assigned, co-pending U.S. patent application Ser. No. 10/002,338 filed Oct. 30, 2001, and Publication No. 2003/0100925. Such mechanical heart function sensors respond to or move with mechanical heart function to derive a metric that changes in value over the heart cycle in proportion to the strength, velocity or range of motion of one or more of the heart chambers or valves. Such a mechanical function metric would complement the measurement of blood pressure and the EGM to more confidently determine the degree of change in an ischemic state or HF condition of the heart.

Turning to FIG. 6, the depicted external programmer 80, patient activator 90, and the drug reservoir, roller pump 244, catheter port 246, and operating system 200 correspond to and function as described above in regard to FIG. 2. Thus, the IM/IIP 250 incorporates the physical structure of the IIP 50 but further includes the input/output circuit 112 of an IHM for receiving and processing EGM signals from one or more of the sense electrodes 72, 74, 162, 164, 166 and powering and processing the ischemia signal of the ischemia monitor 70. It would be expected that the selected EGM electrodes would be programmable by the physician. A patient activity sensor 106 may also be provided in housing 158 to develop an activity signal. The micro-computer-based timing and control system 202 and the input/output circuit 112 perform the dosage adjustment and delivery algorithm depicted in the steps of FIG. 8. In this embodiment, the micro-computer-based timing and control system 202 processes the signals developed in the input output circuit 112 received through data communication bus 130 to perform the steps of FIG. 8.

The general operation of the IHM 50 in performing a dosage adjustment algorithm and communicating an adjusted dosage to the external drug dispenser (or a discrete IIP or IIP function incorporated into a combined IHM and IIP) is set forth in the steps of FIG. 5. The physiologic sensor 70 and the activity sensor 106 are periodically powered to develop sensor output signals and the near field and/or far field EGM signals are periodically sampled by the input/output circuit 112 and provided by bus 130 to the micro-computer-based timing and control system 202. The sensor output and EGM signals are processed in step S200 to calculate the adjusted dosage. The adjusted dosage is compared to the current dosage, that is the most recently determined dosage, and to programmed dosage limits in step S202.

The adjusted dosage is substituted for the current dosage in step S208 if the adjusted dosage differs from the current dosage as determined in step S204 and the adjusted dosage is within programmed limits as determined in step S206. The adjusted dosage that is stored in step S210 with related data for UT transmission to the external programmer 80 may be limited to one of the upper or lower dosage limits in step S208 if the adjusted dosage satisfying step S204 is determined to beyond the programmed limits in step S206.

Thus, the adjusted dosage is stored in RAM for use as the current dosage and for UT transmission upon receipt of a DT transmitted interrogation command from programmer 80. The micro-computer-based timing and control system 202 performs the steps S212 and S214 in the same fashion as steps S100 and S102 of FIG. 4 as described above. Similarly, the micro-computer-based timing and control system 202 performs the steps S216 and S218 in the same fashion as steps S108 and S110 of FIG. 4 as described above. The dosage is delivered in step S218 in the manner of step S110 of FIG. 4 as described above.

It has also been proposed to implant multiple implantable medical devices (IMDs) in the same patient, and to enable communication between the IMDs, whereby the multiple IMDs function cooperatively as disclosed, for example, in commonly assigned U.S. Pat. No. 4,987,897 to Funke. The multiple IMDs include tissue stimulators, e.g., cardiac pacemakers, implantable cardioverter-defibrillators (ICDs), gastro-intestinal stimulators, deep brain stimulators, and spinal cord stimulators, IIPs, implantable physiologic sensors, and activity sensors. Consequently, it will be appreciated that the system and method of the embodiment of FIGS. 6-8 can be alternatively realized employing IIP 50 coupled to infusion catheter 40 and a separately housed and implanted IM having an array of far field sense electrodes 162, 164, 166 and coupled with the ischemia monitoring lead 60. In this case, steps S200-S210 of FIG. 8 would be performed in the IM, and the resulting adjusted dosage would be transmitted to the IIP 50, where it would be stored in IIP RAM for use in performing steps S212-S218.

A variety of patient worn external drug delivery systems have been developed that obviate the problems that arise from patient non-compliance with the prescribed drug regimen, that are convenient to use and enable more precise dosage titration, and that reduce side effects as a result of the dosage titration and because the drug can, in certain cases, be delivered to an optimal delivery site rather than being injected into the blood stream or ingested. Consequently, it will be appreciated that the present invention may be practiced employing an externally worn drug pump in place of the IIP 50 and coupled to infusion catheter 50 extending through a skin incision. It will be further appreciated that the system and method of the embodiment of FIGS. 6-8 can be alternatively realized employing such an external drug pump coupled to infusion catheter 40 and a separately housed and implanted IM having an array of far field sense electrodes 162, 164, 166 and coupled with the ischemia monitoring lead 60. In this case, steps S200-S210 of FIG. 8 would be performed in the IM, and the resulting adjusted dosage would be transmitted to the external drug pump, where it would be stored in IIP RAM for use in performing steps S212-S218.

Figure 9:
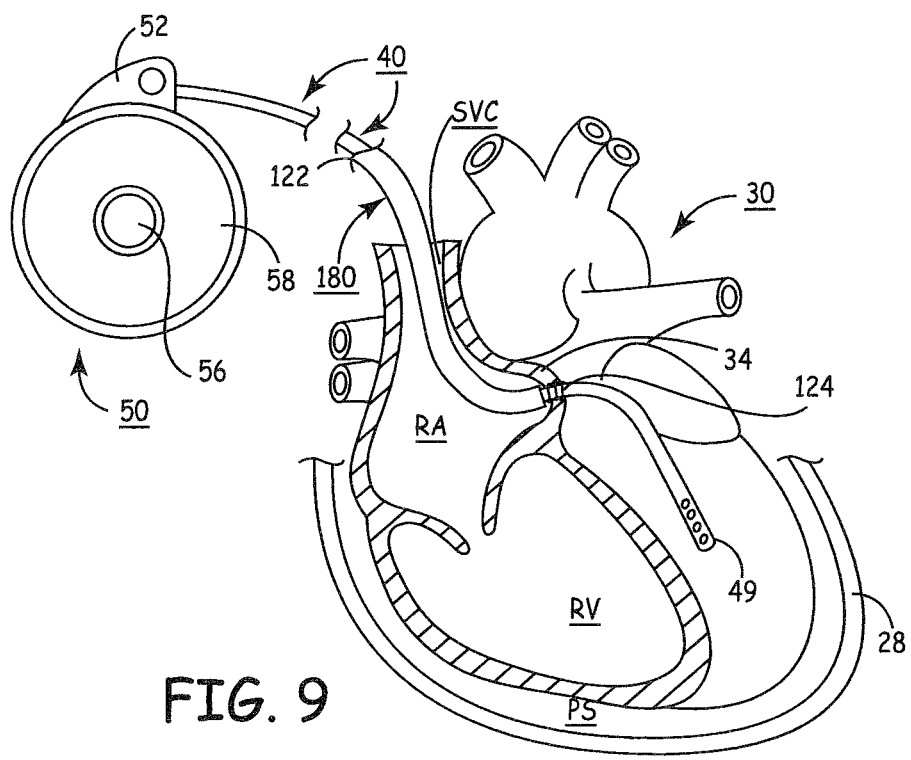
FIG. 9 is a schematic illustration of the exemplary and optional use of a fixation catheter to route the infusion catheter into the pericardial space.

FIG. 9 illustrates a preferred manner of passing the infusion catheter 40 through the right atrial wall to transvenously accessing the pericardial space PS involves passing a fixation catheter 120 having a fixation catheter lumen 122 extending between proximal and distal fixation catheter lumen openings and a distal tissue fixation mechanism 124 through a selected peripheral vein and one of the inferior vena cava and the SVC to establish a transvenous route into the RA. The distal fixation mechanism 124 and distal fixation catheter lumen opening are disposed proximate the right atrial wall 34 in the atrial appendage 36, and the distal fixation mechanism 124 is affixed to the right atrial wall 34. The infusion catheter 40 is passed through the fixation catheter lumen 122 out of the distal fixation catheter lumen opening and through the stabilized atrial wall 34 to dispose the distal catheter segment having the distal infusion catheter exit ports in the pericardial space PS.

Figure 10:
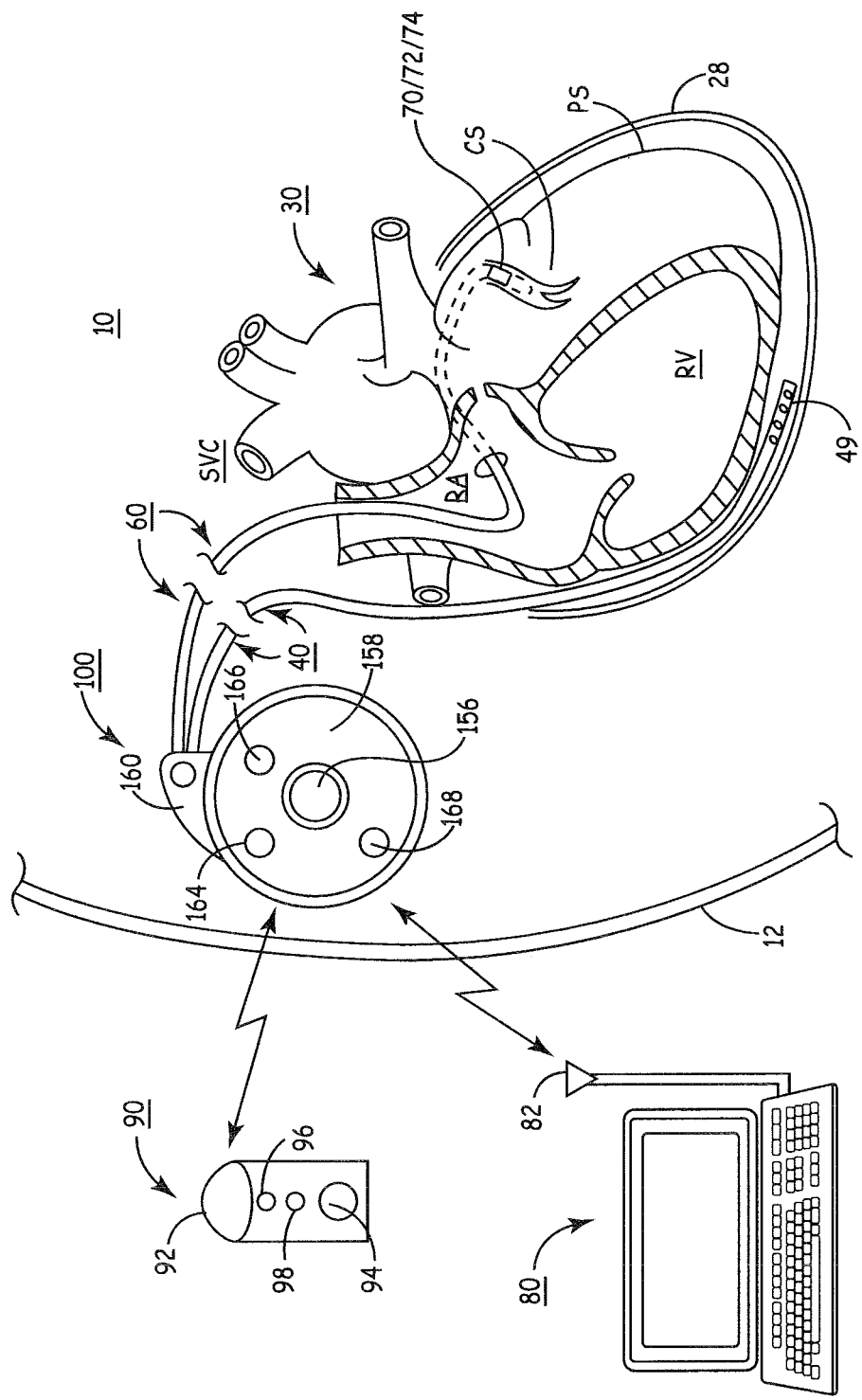
FIG. 10 is a schematic illustration of the operating system of the IIP of FIG. 4 in relation to the external programmer and patient activator with the infusion catheter extending through pericardial sac into the pericardial space.

FIG. 10 illustrates an alternative routing of the infusion catheter 40 through an incision made in the pericardial sac 28 to dispose the exit ports 49 in the pericardial space 49. Access to the pericardial sac 28 may take any form, e.g., those disclosed in the above-referenced '433 patent, and the infusion catheter 40 is routed subcutaneously to the subcutaneously implanted IM/IIP.

Preferably, the pharmacologic agent delivered into the pericardial space as described above comprises NO-releasing or NO-donor drugs preferably selected from the group consisting of nitroglycerin (also known as glyceryltrinitrate or GTN), isosorbide mononitrate (ISMN), sodium nitroprusside (SNP), a diazenium diolate (DETA/NO), NO Aspirins (NCX 4016 and nCX 4215), an S-Nitrosothiol (SNAP), and morpholinosydnonimime (SIN-1). The identification and function of these NO-donor drugs is set forth in "Nitric Oxide Donors" by T. Yamamoto and R. Bing, published in *Proc Soc Exp Biol Med.* 2000 (December; 225(3):200-6) and papers referenced therein. Certain pre-cursors that induce NO production by endothelia NO synthase, e.g., L-arginine, may alternatively be delivered into the pericardial space.

The delivery of the above NO-donor drugs in accordance with the systems and methods of the present invention can be precipitated by a number of events and delivery can be regulated in accordance with a number of scenarios as follows:
1. Acute reversible myocardial ischemia: signs of ischemia via sensor→release of NO-donor until ischemia reverses.
2. Chronic therapy refractory Angina pectoris→signs of ischemia: release of NO-donor until ischemia reverses (effect may be via angiogenesis).
3. Chronic therapy refractory Angina pectoris→patient has angina at rest and activates pump to release of NO-donor until pain reverses.
4. Chronic therapy refractory Angina pectoris→patient is prepared to undergo physical activity and activates release of NO-donor to prevent activity induced angina attacks. The release is timed and so depending on activity duration the patient may need to activate release several times. The release duration is programmable.
5. Acute, subacute myocardial infarction: sensor: biochemical (key=enzyme leakage—prolonged lactate elevation>30 minutes continuously).→infusion of NO-donor during ischemia and reperfusion, possibly up to days to weeks after infarction.
6. If stenting: continuous high-dose NO-donor delivery for days to weeks to prevent in stent restenosis.
7. If TPA treatment: continuous NO-donor delivery to treat ischemia/reperfusion related complications (arrhythmias, stunning, accelerated cell death, infarct expansion).
8. Silent ischemia: ischemia sensor senses ischemia: release of NO-donor until ischemia subsides.
9. Vasospastic Angina: ischemia sensor (typically via ST segment changes) triggers release of NO-donor until ischemia subsides.

Thus, a variety of embodiments are presented that facilitate detecting symptoms of pathologies associated with ischemia and triggering delivery of a pharmacologic agent to a pericardial space site to alleviate such symptoms and otherwise treat ischemia and pathologies associated with ischemia. Moreover, systems and methods for detecting and responding to cardiac conditions by delivering NO-donor drugs into he pericardial space are disclosed.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice.

It is to be understood, that within the scope of the appended claims, the invention may be practiced otherwise than as specifically described without actually departing from the spirit and scope of the present invention. The disclosed embodiments are presented for purposes of illustration and not limitation, and the present invention is limited only by the claims that follow.

What is claimed is:

1. A method of accessing the pericardial space between a heart and its pericardium to deliver a pharmacologic agent for the treatment of ischemia to the heart, the method comprising the steps of:
   advancing an infusion catheter to dispose a distal catheter segment having a distal infusion catheter lumen end opening in the pericardial space;
   attaching a proximal connector of the infusion catheter to an infusion pump having a reservoir containing the pharmacologic agent;
   detecting an ischemic state of the heart; and
   delivering the pharmacologic agent for the treatment of ischemia from the reservoir into the pericardial space to counter the detected ischemic state.

2. The method of claim 1, further comprising:
   detecting a remotely transmitted therapy delivery command; and
   delivering a bolus of the pharmacologic agent.

3. The method of claim 2, wherein the pharmacologic agent comprises NO-donor drugs selected from the group consisting of nitroglycerin, isosorbide mononitrate, sodium nitroprusside, a diazenium diolate, an NO aspirin, an S-Nitrosothiol, morpholinosydnonimime and L-arginin.

4. The method of claim 1, wherein the detecting step comprises:
   sensing a feature of the EGM of the heart; and
   detecting a characteristic of the sensed feature indicative of the ischemic state.

5. The method of claim 4, wherein the pharmacologic agent comprises NO-donor drugs selected from the group consisting of nitroglycerin, isosorbide mononitrate, sodium nitroprusside, a diazenium diolate, an NO aspirin, an S-Nitrosothiol, morpholinosydnonimime and L-arginin.

6. The method of claim 1, wherein the detecting step comprises:
   sensing blood pH; and
   detecting a value of the sensed blood pH indicative of the ischemic state.

7. The method of claim 6, wherein the pharmacologic agent comprises NO-donor drugs selected from the group consisting of nitroglycerin, isosorbide mononitrate, sodium nitroprusside, a diazenium diolate, an NO aspirin, an S-Nitrosothiol, morpholinosydnonimime and L-arginin.

8. The method of claim 1, wherein the detecting step comprises:

sensing blood oxygen saturation; and
detecting a value of the sensed oxygen saturation indicative of the ischemic state.

9. The method of claim 8, wherein the pharmacologic agent comprises NO-donor drugs selected from the group consisting of nitroglycerin, isosorbide mononitrate, sodium nitroprusside, a diazenium diolate, an NO aspirin, an S-Nitrosothiol, morpholinosydnonimime and L-arginin.

10. The method of claim 1, wherein the detecting step comprises:
sensing one or both of blood pressure and flow in the heart; and
detecting a value of the sensed one or both of blood pressure and flow indicative of the ischemic state.

11. The method of claim 10, wherein the pharmacologic agent comprises NO-donor drugs selected from the group consisting of nitroglycerin, isosorbide mononitrate, sodium nitroprusside, a diazenium diolate, an NO aspirin, an S-Nitrosothiol, morpholinosydnonimime and L-arginin.

12. A method of transvenously accessing the pericardial space between a heart and its pericardium to deliver a NO-donor drug to the heart, the method comprising the steps of:
advancing an infusion catheter to dispose a distal catheter segment having a distal infusion catheter lumen end opening in the pericardial space;
attaching a proximal connector of the infusion catheter to an infusion pump;
detecting a condition of the heart; and
delivering a bolus of NO-donor drug.

13. The method of claim 12, further comprising:
detecting a remotely transmitted therapy delivery command; and
delivering a bolus of the NO-donor drug.

14. The method of claim 12, wherein the detecting step comprises:
sensing a feature of the EGM of the heart; and
detecting a characteristic of the sensed feature indicative of an ischemic state.

15. The method of claim 12, wherein the detecting step comprises:
sensing blood pH; and
detecting a value of the sensed blood pH indicative of an ischemic state.

16. The method of claim 12, wherein the detecting step comprises:
sensing blood oxygen saturation; and
detecting a value of the sensed oxygen saturation indicative of an ischemic state.

17. The method of claim 12, wherein the detecting step comprises:
sensing one or both of blood pressure and flow in the heart; and
detecting a value of the sensed one or both of blood pressure and flow indicative of an ischemic state.

18. The method of claim 12, wherein the advancing step comprises:
passing a fixation catheter having a fixation catheter lumen extending between proximal and distal fixation catheter lumen openings and a distal tissue fixation mechanism through a selected peripheral vein and one of the inferior vena cava and the superior vena cava to establish a transvenous route into the right atrium of the heart
disposing the distal fixation mechanism and distal fixation catheter lumen opening proximate the right atrial wall;
affixing the distal fixation mechanism to the right atrial wall;
passing an infusion catheter through the fixation catheter lumen out of the distal fixation catheter lumen opening and through the stabilized atrial wall to dispose a distal catheter segment having a distal infusion catheter lumen end opening in the pericardial space.

19. The method of claim 12, wherein the advancing step comprises advancing the distal catheter segment from the right atrium through the right atrial wall.

20. The method of claim 12, wherein the NO-donor drug is selected from the group consisting of nitroglycerin, isosorbide mononitrate, sodium nitroprusside, a diazenium diolate, an NO aspirin, an S-Nitrosothiol, morpholinosydnonimime and L-arginin.

21. The method of claim 1, wherein detecting an ischemic state of the heart comprises detecting acute reversible myocardial ischemia, chronic therapy refractory angina pectoris, acute myocardial infarction, subacute myocardial infarction, silent ischemia, or vasospastic angina.

22. The method of claim 12, wherein detecting a condition of the heart comprises detecting acute reversible myocardial ischemia, chronic therapy refractory angina pectoris, acute myocardial infarction, subacute myocardial infarction, silent ischemia, or vasospastic angina.

* * * * *